United States Patent [19]

Shigyo et al.

[11] Patent Number: 5,231,572
[45] Date of Patent: Jul. 27, 1993

[54] RADIATION IMAGE STORAGE AND REPRODUCTION SYSTEM

[75] Inventors: Masao Shigyo; Eiichi Asai, both of Kanagawa, Japan

[73] Assignee: Fuji Photo Film Co., Ltd., Kanagawa, Japan

[21] Appl. No.: 704,716

[22] Filed: May 20, 1991

Related U.S. Application Data

[63] Continuation of Ser. No. 544,099, Jun. 26, 1990, abandoned, which is a continuation of Ser. No. 110,402, Oct. 20, 1987, abandoned.

[30] Foreign Application Priority Data

| Oct. 20, 1986 | [JP] | Japan | 61-248853 |
| Oct. 20, 1986 | [JP] | Japan | 61-248854 |
| Oct. 20, 1986 | [JP] | Japan | 61-248855 |

[51] Int. Cl.$^5$ ............ G06F 15/42; G06F 15/62; G06F 15/66
[52] U.S. Cl. ............ 364/413.01; 364/413.13; 358/111; 358/448
[58] Field of Search ............ 364/413.01, 413.13, 364/413.22, 413.23; 358/448, 111

[56] References Cited

U.S. PATENT DOCUMENTS

| 4,611,247 | 9/1986 | Ishida et al. | 364/414 X |
| 4,641,242 | 2/1987 | Kimura | 364/414 |
| 4,653,112 | 3/1987 | Ouimette | 364/413.22 X |
| 4,739,480 | 4/1988 | Oono et al. | 364/414 |
| 4,833,625 | 5/1989 | Fisher et al. | 364/518 |
| 4,887,211 | 12/1989 | Thiel et al. | 364/413.13 |
| 4,910,607 | 3/1990 | Kita et al. | 358/448 |

Primary Examiner—Roy N. Envall, Jr.
Assistant Examiner—Jennifer L. Hazard
Attorney, Agent, or Firm—Sughrue, Mion, Zinn, Macpeak & Seas

[57] ABSTRACT

A radiation image storage and reproduction system includes a radiation image read-out device for reading out a radiation image stored in a stimulable phosphor sheet to obtain digital image data of the radiation image; an image-concomitant information input device for inputting information of a forwarding address and/or an information of a image processing operation for the digital image data; an image processing device for processing the digital image data; a display device for visually reproducing the radiation image from the digital image data; and an image filing device for storing the digital image data. In one embodiment all of the above devices are connected to an image forwarding-processing controller device for deciding a forwarding address of the digital image data based on the information of the forwarding address and for forwarding the digital image data to the decided address and/or for deciding a processing or processing to be applied to the digital image data based on the information of the image processing operation.

10 Claims, 8 Drawing Sheets

RADIATION IMAGE STORAGE AND REPRODUCTION SYSTEM

This is a continuation of application Ser. No. 07/544,099 filed Jun. 26, 1990, now abandoned, which is a continuation of application Ser. No. 07/110,402, filed Oct. 20, 1987 abandoned.

BACKGROUND OF THE INVENTION

1. Field of the invention

This invention relates to a radiation image storage and reproduction system, and more particularly to a radiation image storage and reproduction system utilizing a stimulable phosphor sheet.

2. Description of prior art

A radiation image storage and reproduction method using a stimulable phosphor has been recently developed for replacing the conventional radiographic process. For instance, the radiation image storage and reproduction method is described in U.S. Pat. No. 4,239,968 and Japanese Patent Provisional Publications No. 55(1980)-12429, No. 55(1980)-87970, No. 55(1980)-103472, and No. 55(1980)-116340.

The stimulable phosphor absorbs and stores a radiation such as X-rays applied thereto and then emits the stored radiation energy in the form of a stimulated emission when it is irradiated with stimulating rays such as visible rays. The radiation image storage and reproduction method comprises the steps of causing a stimulable phosphor sheet (also referred to as radiation image storage panel or imaging plate) containing the stimulable phosphor to absorb radiation energy having passed through an object or having radiated from an object; sequentially exciting the stimulable phosphor with an electromagnetic wave such as visible rays or infrared rays (referred to as "stimulating rays") to release the radiation energy stored in the phosphor as light emission (stimulated emission); photoelectrically detecting the emitted light to obtain electric signals; and converting the electric signals into digital signals through analogue/digital (A/D) conversion. The obtained digital signals corresponding to the radiation image is optionally processed by one or more image processing methods, and reproduced as a visible image on a photographic material and/or stored in a memory means such as a magnetic tape or an optical disc.

Using the radiation image recording and reproducing method, a radiation image is obtainable with a sufficient amount of information by applying a radiation to an object at considerably smaller dose, as compared with the conventional radiography. Further, since the radiation image information can be directly obtained in the form of digital signals, various advantageous effects are attained. For instance, image processing such as gradation or contrast control processing can be readily performed; the image information can be reproduced in an optionally chosen form; and the information can be easily and reliably stored. Accordingly, this method is of great value in various radiographic processes, especially when the method is used for medical diagnosis.

The known radiation image recording and reproducing method is performed using various systems using several devices such as a radiation image read-out means for reading out a radiation image stored in a stimulable phosphor sheet to obtain digital image data of the radiation image; an image-concomitant information input means for inputting an information of forwarding address and/or an information (and optionally other data) of image processing operation for the digital image data; and image processing means for processing the digital image data; a display means for visually reproducing the radiation image from the digital image data; and an image filing means for storing the digital image data. Examples of the systems include an image reproducing system comprising a radiation image read-out apparatus, an image-concomitant information input apparatus, an image processing apparatus and a display apparatus; an image data storing system comprising a radiation image read-out apparatus, an image-concomitant information input apparatus, an image processing apparatus and an image filing apparatus; or a stored-image data out-put system comprising an image filing apparatus, an image processing apparatus and a display apparatus.

SUMMARY OF THE INVENTION

It is an object of the present invention to provide a system advantageously employable for performing the radiation image storage and reproduction method utilizing a stimulable phosphor.

It is another object of the invention to provide a system efficiently and easily employable for performing the radiation image storage and reproduction method.

It is a further object of the invention to provide a system reliably employable for performing the radiation image storage and reproduction method.

It is a still further object of the invention to provide a system economically employable for performing the radiation image storage and reproduction method.

There is provided by the present invention a radiation image storage and reproduction system comprising:

a radiation image read-out means for reading out a radiation image stored in a stimulable phosphor sheet to obtain digital image data of the radiation image;

an image-concomitant information input means for imputting an information of forwarding address and/or an information of image processing operation for the digital image data;

an image processing means for processing the digital image data;

a display means for visually reproducing the radiation image from the digital image data; and an image filing means for storing the digital image data, all means being connected to an image forwarding-processing controller means for controlling operations to decide a forwarding address of the digital image data based on the information of forwarding address and forward the digital image data to the decided address and/or to decide a processing to be applied to the digital image data based on the information of image processing operation.

In the above-described radiation image storage and reproduction system, the image-concomitant information input means can be connected not to the image forwarding-processing controller means but to the radiation image read-out means, whereby the image-concomitant information (i.e., information relating to the radiation image which is read out from the stimulable phosphor sheet) is first supplied to the radiation image read-out means and then the image-concomitant information is supplied to the image forwarding-processing controller means together with the digital image data of the radiation image which was stored and read out from the stimulable phosphor sheet.

There is also provided by the present invention a radiation image storage and reproduction system comprising:
- the radiation image read-out means;
- the image-concomitant information input means;
- a plurality of the image processing means;
- the display means; and
- the image filing means,
  said plurality of image processing means being connected to the image forwarding-processing controller means.

According to the radiation image storage and reproduction system of the invention, various apparatuses preferably provided for performing the radiation image recording and reproducing method, such as the radiation image read-out means, the image-concomitant information input means, the image processing means, a display means, and an image filing means are efficiently connected directly or indirectly to an image forwarding-processing controller means for controlling operations to decide a forwarding address of the digital image data based on the information of forwarding address and forward the digital image data to the decided address and/or to decide a processing or processings to be applied to the digital image data based on the information of image processing operation. Therefore, in the radiation image storage and reproduction system of the invention, an image reproducing system comprising a radiation image read-out apparatus, an image-concomitant information input apparatus, an image processing apparatus and a display apparatus, an image data storing system comprising a radiation image read-out apparatus, an image-concomitant information input apparatus, an image processing apparatus and an image filing apparatus, and a stored-image data output system comprising an image filing apparatus, an image processing apparatus and a display apparatus which have been heretofore installed independently of each other are efficiently and economically combined in one system. Accordingly, a simple controlling operation utilizing the image-concomitant information input means and the image forwarding-processing controller means enables to perform visualizing the radiation image, processing the radiation image data and storing the digital image data at an optional stage and in an optional order.

DETAILED DESCRIPTION OF THE INVENTION

The present invention is described in more detail by referring to the accompanying drawings.

Figure 1:
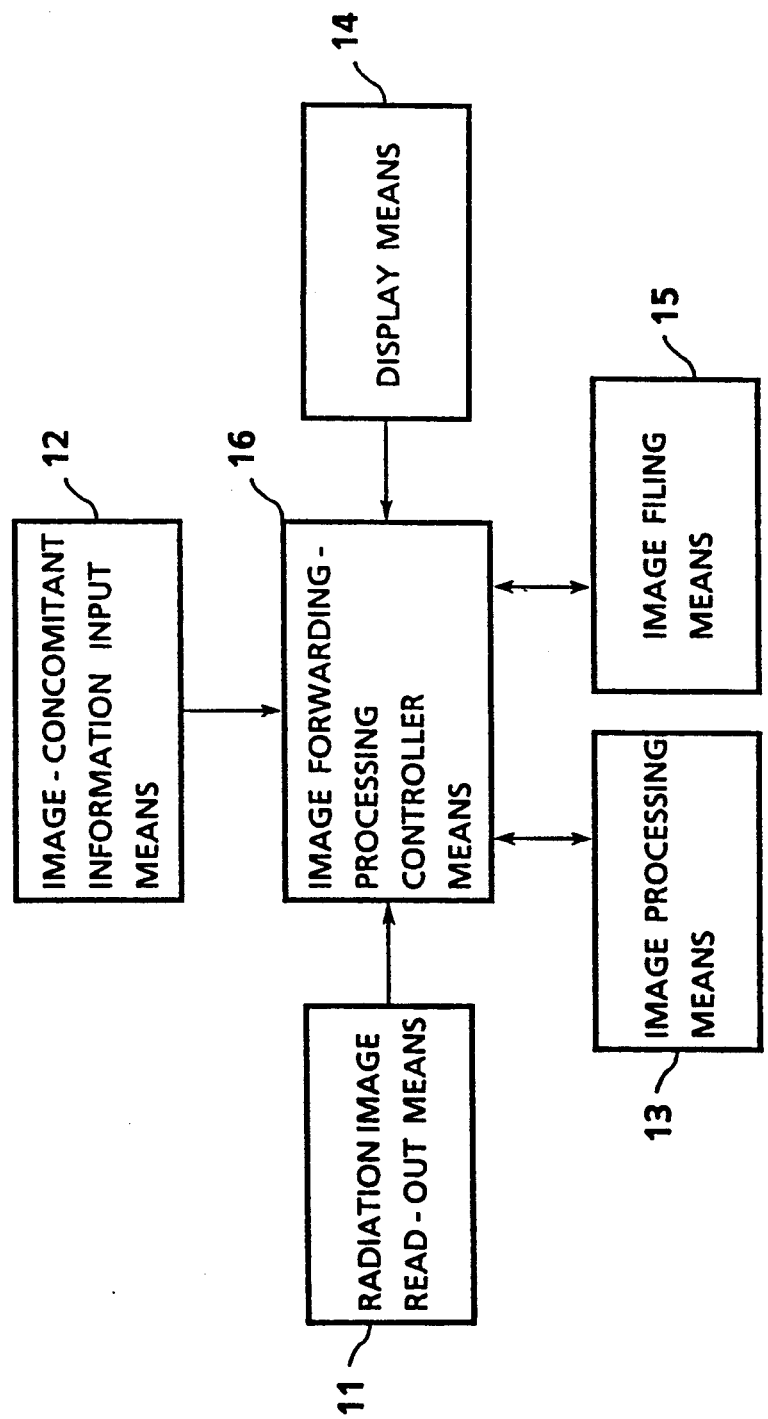
FIG. 1 is a block diagram showing one embodiment of the radiation image storage and reproduction system of the present invention.

As is illustrated in FIG. 1, the first embodiment of the radiation image storage and reproduction system of the invention comprises:
- a radiation image read-out means 11 for reading out a radiation image stored in a stimulable phosphor sheet to obtain digital image data of the radiation image;
- an image-concomitant information input means 12 for inputting an information of forwarding address and/or an information of image processing operation for the digital image data obtained from the stimulable phosphor sheet in the radiation image read-out means 11;
- an image processing means 13 for processing the digital image data;
- a display means 14 for visually reproducing the radiation image from the digital image data;
- an image filing means 15 for storing the digital image data; and
- an image forwarding-processing controller means 16 which controls operations to decide a forwarding address of the digital image data based on the information of forwarding address and forward the digital image data to the decided address and/or to decide a processing to be applied to the digital image data based on the information of image processing operation.

The radiation image read-out means 11, the image-concomitant information input means 12, the image processing means 13, the display means 14 and the image filing means 15 all are connected to the image forwarding-processing controller means 16.

The radiation image read-out means 11, the image-concomitant information input means 12, the image processing means 13, the display means 14, the image filing means 15, and the image forwarding-processing controller means 16 can all be provided to the system in plural numbers. Particularly, radiation image read-out means 11, the image processing means 13, the display means 14, and the image filing means 15 are advantageously provided to the system in two or more numbers.

Figure 2:
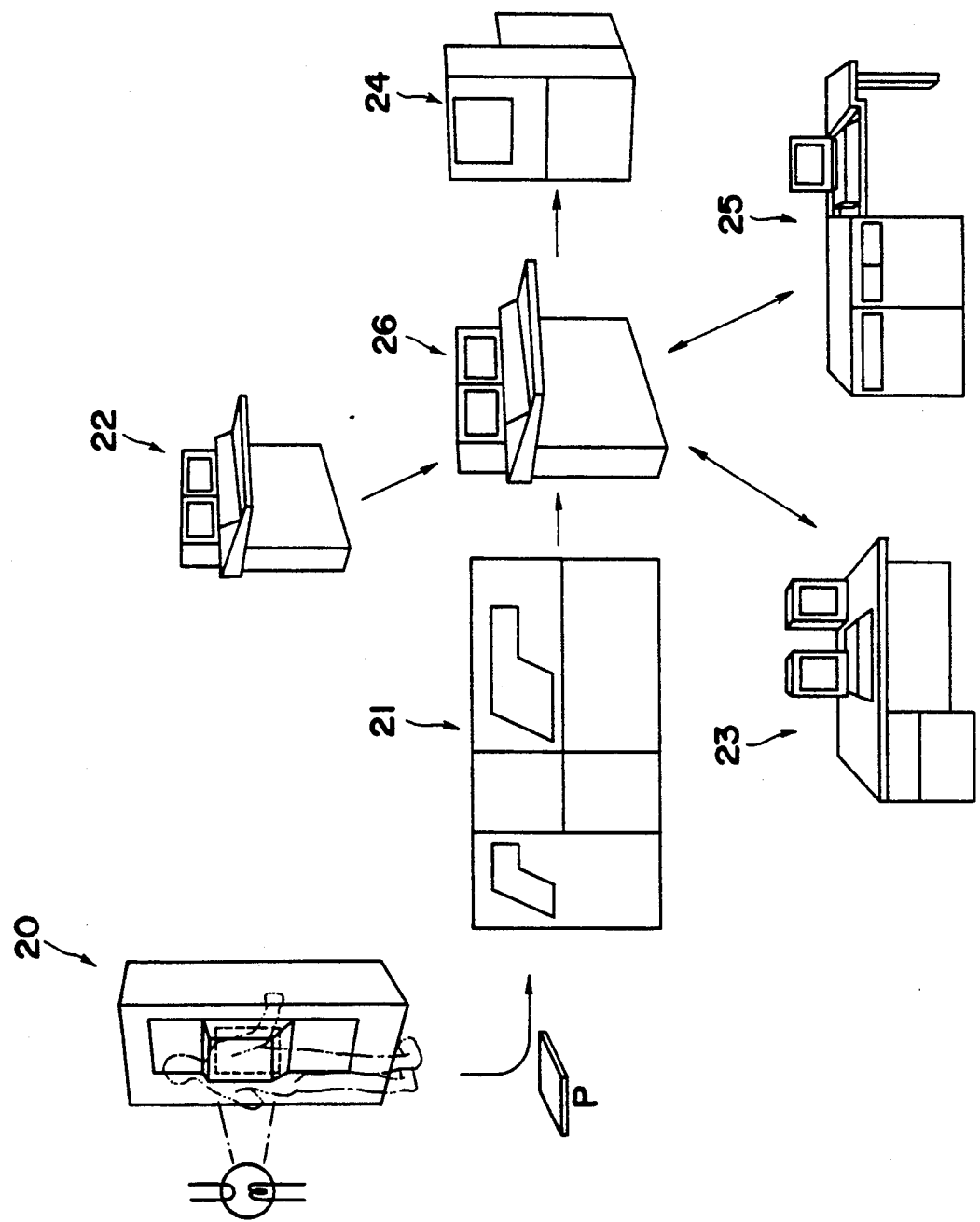
FIG. 2 shows one of examples of the arrangement of the radiation image storage and reproduction system indicated in FIG. 1.

An example of practical arrangement for the radiation image storage and reproduction system of FIG. 1 is illustrated in FIG. 2.

A man (patient) is exposed to radiation of X-rays in a radiographic apparatus 20, and a radiographic image of the patient is recorded on a stimulable phosphor sheet (P). The stimulable phosphor sheet (P) is then transferred to a radiation image read-out apparatus 21 for reading out a radiation image stored in the stimulable phosphor sheet to obtain digital image data of the radiation image.

The radiation image read-out apparatus 21 comprises, for instance, a stacker for a plurality of stimulable phosphor sheets; a read-out device for scanning stimulating rays such as a laser beam on the stimulable phosphor sheets to stimulate the phosphor in the sheet so as to emit a stimulated emission, and detecting photoelectrically the stimulated emission; an erasure device for removing residual radiation energy from the phosphor sheet; and a set of conveyors for transferring the phosphor sheet to appropriate devices. The detected stimulated emission contains the radiation image information and is processed by an A/D converter to give digital image data of the radiation image information. A variety of constitutions of the radiation image read-out apparatus are already known. Alternatively, the radiographic apparatus and the radiation image read-out apparatus can be combined in one unit to give a built-in type apparatus.

The digital image data are transferred to the image forwarding-controlling controller 26.

Separately, a variety of supplemental information such as clinical information, an information of forwarding address and an information of image processing operation relating to the radiation image information which is now converted into digital image data are input in an image-concomitant information input apparatus 22. Examples of the information include date and place for the radiographic operations involved, exposed positions, ID number, name, age, sex and the like, of the exposed patient (exposed object). Examples of the information of forwarding address include instructions for forwarding address such as instructions to designate one or more apparata to which the radiation image data should be supplied, instructions on whether the image data should be stored or not, instructions on whether the image data should be compacted or concentrated prior to storage in the image filing apparatus, and instructions on whether the radiation image is printed or not in the display apparatus. Examples of the information of image processing operation include instructions to perform substruction operation, energy substruction operation, enlargement, compression and optional combinations of these operations.

The operation for inputting the supplemental information can be performed by automatically reading out the information from an ID card (identification card) or the stimulable phosphor sheet employed for the radiographic operation using an optical read-out device. Alternatively, the supplemental information can be manually input in the apparatus 22 by an operator using a key board, based on a visual data produced on a display such as CRT. The operation for the input can be performed utilizing an optional combination of a variety of known operations. The supplemental information is then forwarded to the image information forwarding-processing controller 26.

The image information forwarding-processing controller 26 decides or determines forwarding address of the image digital data and/or processing operations to be applied to the digital data, by referring to the supplemental information forwarded from the image-concomitant information input apparatus 22. According to the decisions, the image digital data are transferred to one or more of an image processing apparatus 23, a display apparatus 24 and an image filing apparatus 24. The image digital data can be forwarded to only a single apparatus, or to two or more apparatuses. Further, one or more out of a plural image processing apparatuses, display apparatuses, etc. can be chosen as the forwarding address.

The image processing apparatus 23 has the function of processing the forwarded digital data, for example, to give an appropriate image which is well acceptable for visual inspection. A variety of image processings can be performed in the image processing apparatus 23 according to the instructions which have been produced in the image forwarding-processing controller 26 in consideration of the supplemental information for the radiation image information supplied from the radiation image read-out apparatus 21. Examples of the image processings include relatively simple processings such as gradation or contrast controlling, frequency processing, addition-averaging, enlarging and compressing and relatively complicated processing such as subtraction for an angiocardiographic image and an tomographic image. The image processing can be done singly, or a combination of different image processings can be performed using one or more image processing apparatuses. A plurality of same or different processing apparatuses can be used.

The image processing operation can be performed at an optional stage. For instance, the image processing operation is performed prior to, simultaneously with or after storing the digital image data in the image filing apparatus 23 or reproducing the radiation image on the display apparatus 24. The processed digital image data are then returned to the image forwarding-processing controller 26 and forwarded to other apparatuses such as the display apparatus 24 and the image filing apparatus 25.

The image filing apparatus 25 receives the processed or unprocessed digital image data forwarded from the image forwarding-processing controller 26. In advance of storing the forwarded data, the data can be converted in the image filing apparatus into compacted data which are efficiently stored in the filing apparatus 25.

A representative example of the image filing apparatus 25 is an optical disc filing apparatus. An example of the optical disc filing apparatus comprises an optical disc for storing the digital image data, a control device for storage and reference of the image data, a magnetic disc for storing supplemental information of the image data and other information for the image data for searching the image data at a later stage, a CRT (cathode ray tube) display for searching the data, and a key board. The image filing apparatus may be provided with other functions such as a function for processing the digital image data for zone compression, a function for reviving the compressed image data when the data are reproduced as a visible image, and a function for retrieving the stored image. The image storing apparatus using an optical disc is very advantageous because the optical disc stores a large amount of data in a small-sized space. Further, the storage of supplemental information and data separately in a magnetic disc is advantageous, because such arrangement is effective for efficiently performing data retrieval in a short period of time. However, the image filing apparatus is not limited to an apparatus using an optical disc, as, any of other storing or recording means can be employed.

When the stored digital image data are to be reproduced on the display apparatus 24, the stored data are returned, if necessary after modifying or reviving the compressed data in the form of the uncompressed digital image data, to the image forwarding-processing controller 26 and forwarded to the display apparatus 24.

The display apparatus 24 generally comprises an exposing device for recording an image on a photographic film by scanning a laser beam on the film and a developing device for developing the exposed film. The display apparatus can be charged with a number of photographic films. However, the display apparatus is not limited to the apparatus for producing such a photographic image. For example, the display apparatus can be an apparatus for recording an image on a heat sensitive material using thermic rays, an apparatus for recording an image on a photosensitive paper using an optical means, or a CRT display means.

Figure 3:
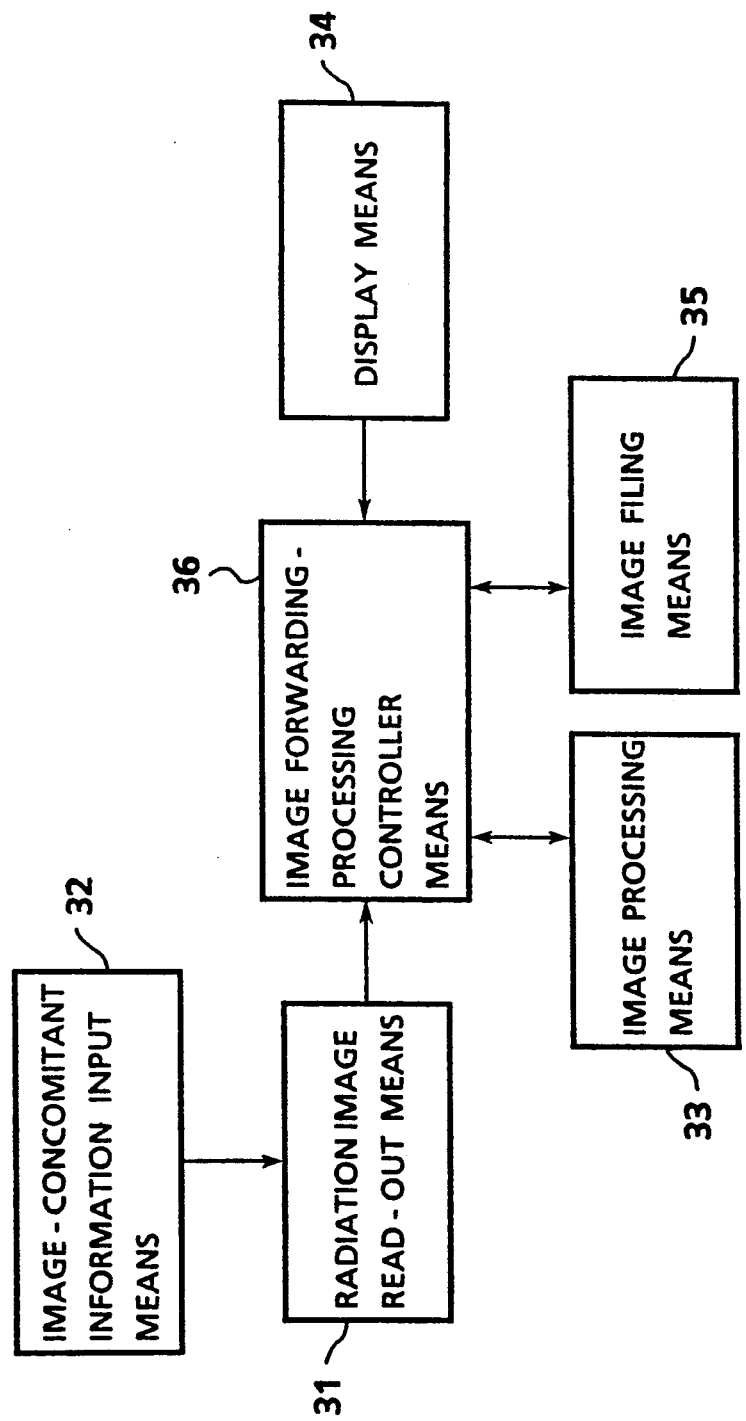
FIG. 3 is a block diagram showing another embodiment of the radiation image storage and reproduction system of the present invention.

As described hereinbefore, the image-concomitant information input apparatus can be connected to the radiation image read-out apparatus. Such system is illustrated in FIG. 3 as a block diagram. In the block diagram, an image-concomitant information input means 32 is connected to a radiation image read-out means 31. The read-out means 31 is connected to an image forwarding-processing controller means 36. To the image forwarding-processing controller means 36 are connected an image processing means 33, a display means 34, and an image filing means 35. In this system, the supplemental information is supplied to the controller means 36 together with the digital image data obtained in the read-out means 31.

Alternatively, the image-concomitant information input means can be connected to both the radiation image read-out means and the image forwarding-processing controller means.

FIGS. 4–7 illustrate other embodiments of the radiation image storage and reproduction system according to the invention, which comprise the radiation image read-out means; the image-concomitant information input means; a plurality of the image processing means; the display means; and the image filing means. The plurality of image processing means are connected to the image forwarding-processing controller means.

Figure 4:
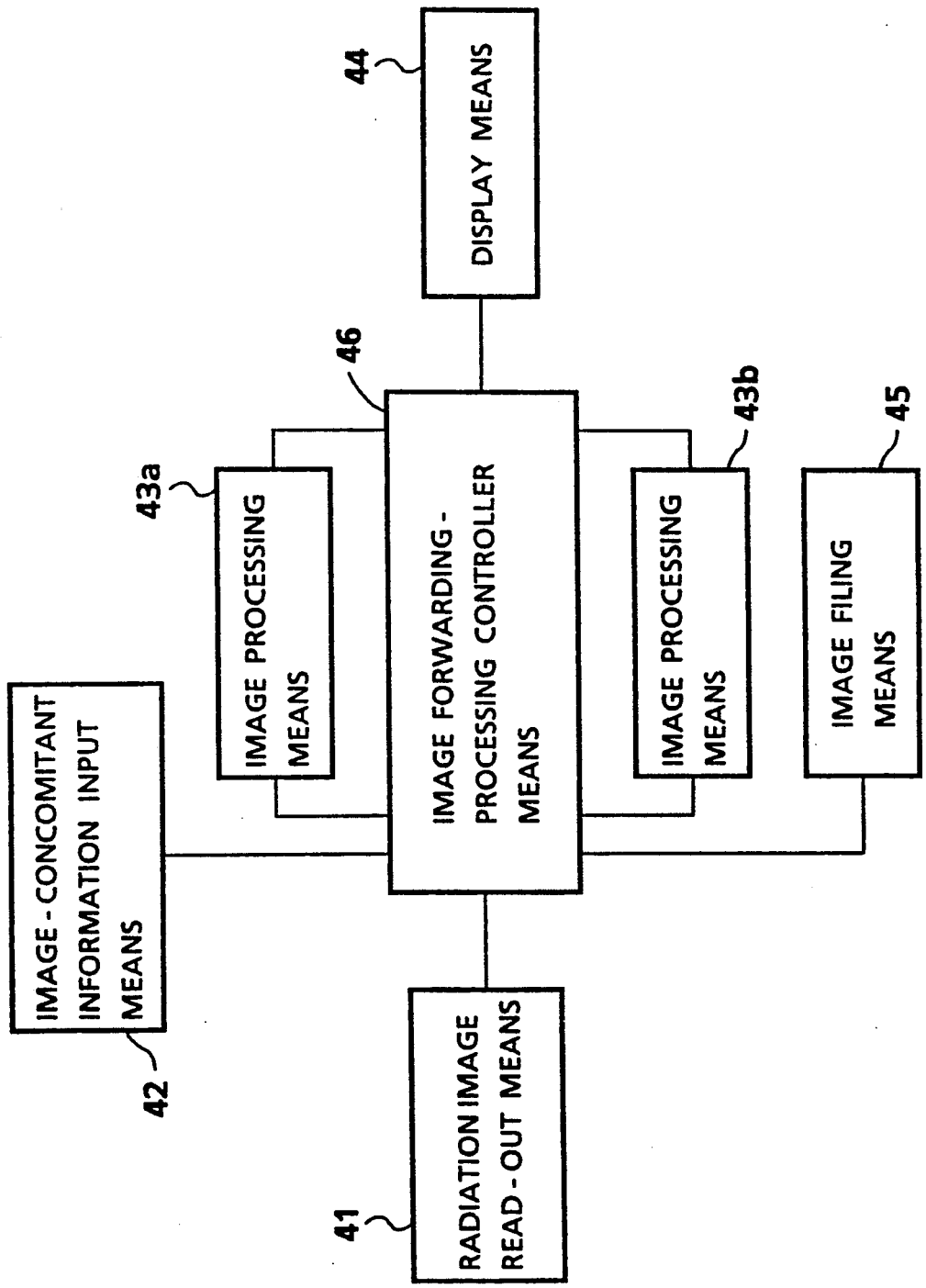
FIG. 4 is a block diagram showing a further embodiment of the radiation image storage and reproduction system of the present invention.

In the system of FIG. 4, the radiation image read-out means 41, the image-concomitant information input means 42, two image processing means 43a, 43b, the display means 44, and the image filing means 45 are connected to the image forwarding-processing controller means 46. The two image processing means 43a, 43b are the same or different from each other in their function. For instance, the image processing means 43a is provided for relatively complicated processing, while the image processing means 43b is for relatively simple processing.

Figure 5:
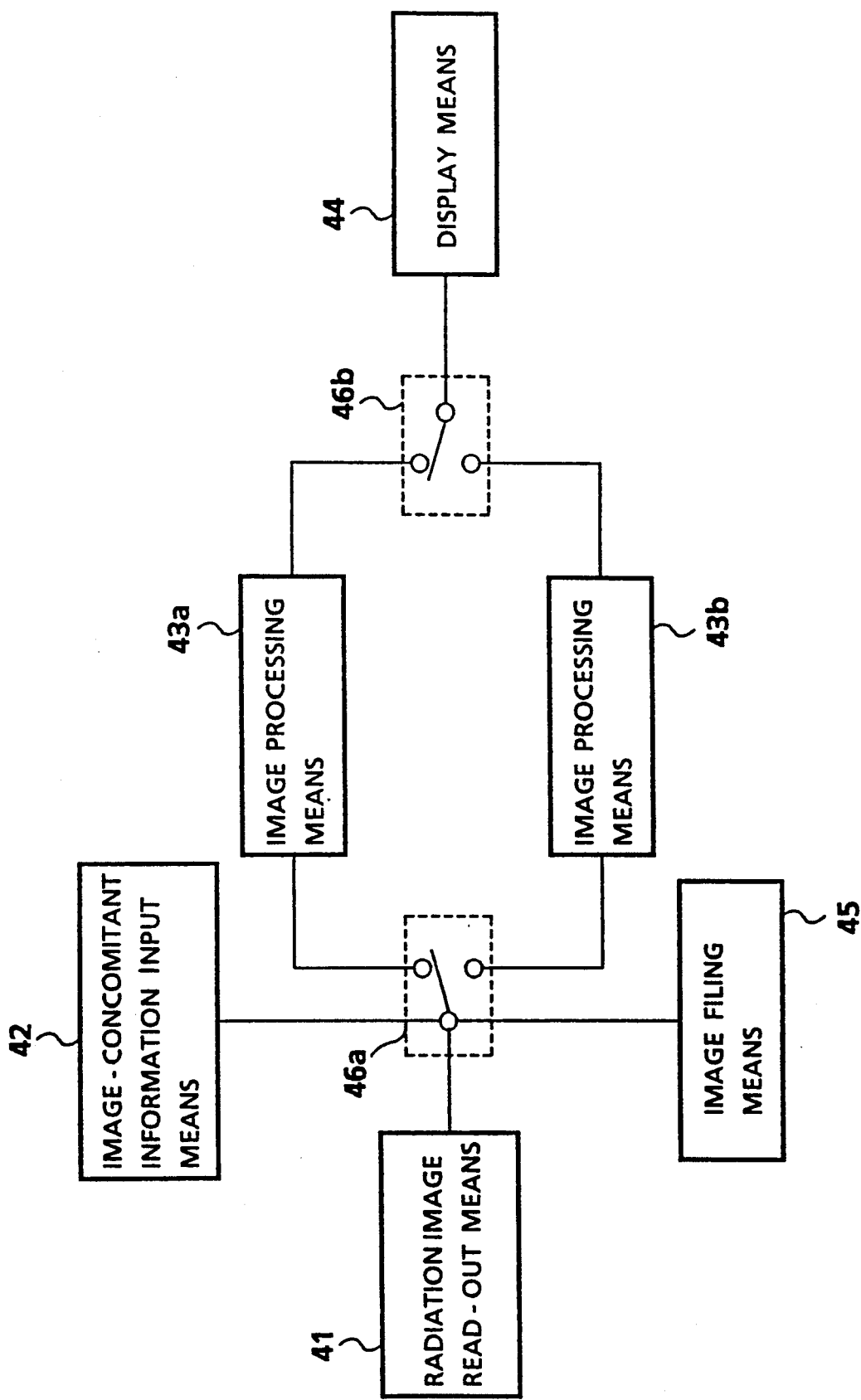
FIG. 5 is a block diagram illustrating the image forwarding-processing controller of FIG. 4 in more detail.

FIG. 5 schematically illustrates more concretely the function of the image forwarding-processing controller means wherein the controller means 46 are divided into two units 46a, 46b. When digital image data and their supplemental data are supplied from the read-out means 41 and the image-concominant information input means 42, respectively, to the controller unit 46a, the controller unit 46a studies these data and decides where the digital image data should be forwarded. For instance, the digital image data are forwarded to the image filing means 45 for storing therein, as well as to the image processing means 43a for appropriate processing. The digital image data are processed in the image processing means 43a and then forwarded through the unit 46b to the display means 44. Naturally, other routes for forwarding and processing the digital image data can be chosen.

The provision of the plurality of image processing means to the system is very advantageous because if one of the processing means is damaged, another means can be used for data processing without stopping the operation of the system.

Figure 6:
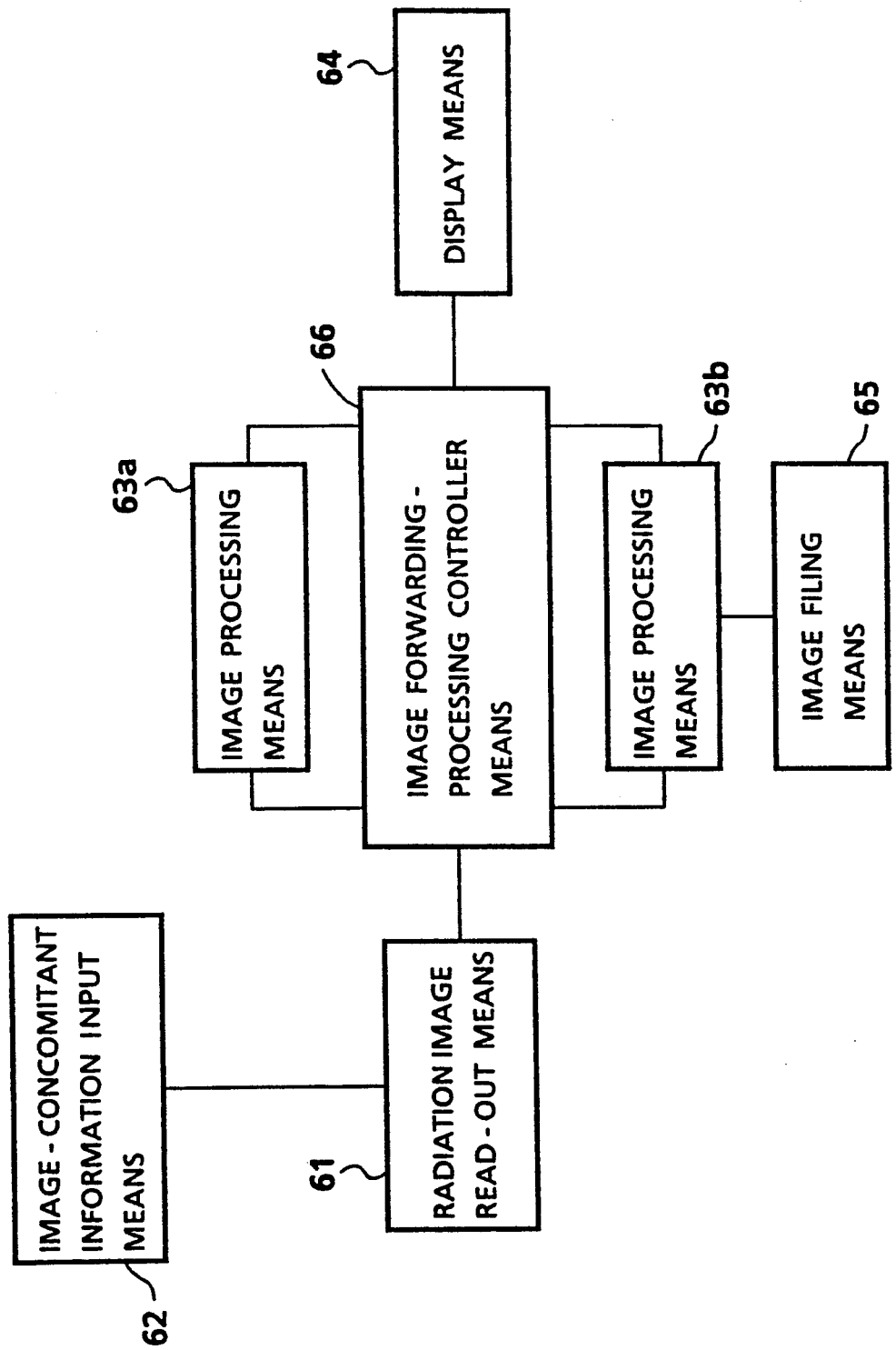
FIG. 6 is a block diagram showing a further embodiment of the radiation image storage and reproduction system of the present invention.

In the system of FIG. 6, the radiation image read-out means 61, two image processing means 63a, 63b, and the display means 64 are connected to the image forwarding-processing controller means 66. The image-concomitant information input means 62 is connected to the radiation image read-out means 61, as in the case illustrated in FIG. 3. The image filing means 65 is connected to one image processing means 63b. The two image processing means 63a, 63b are the same or different from each other in their function, as is the case illustrated in FIG. 4.

Figure 7:
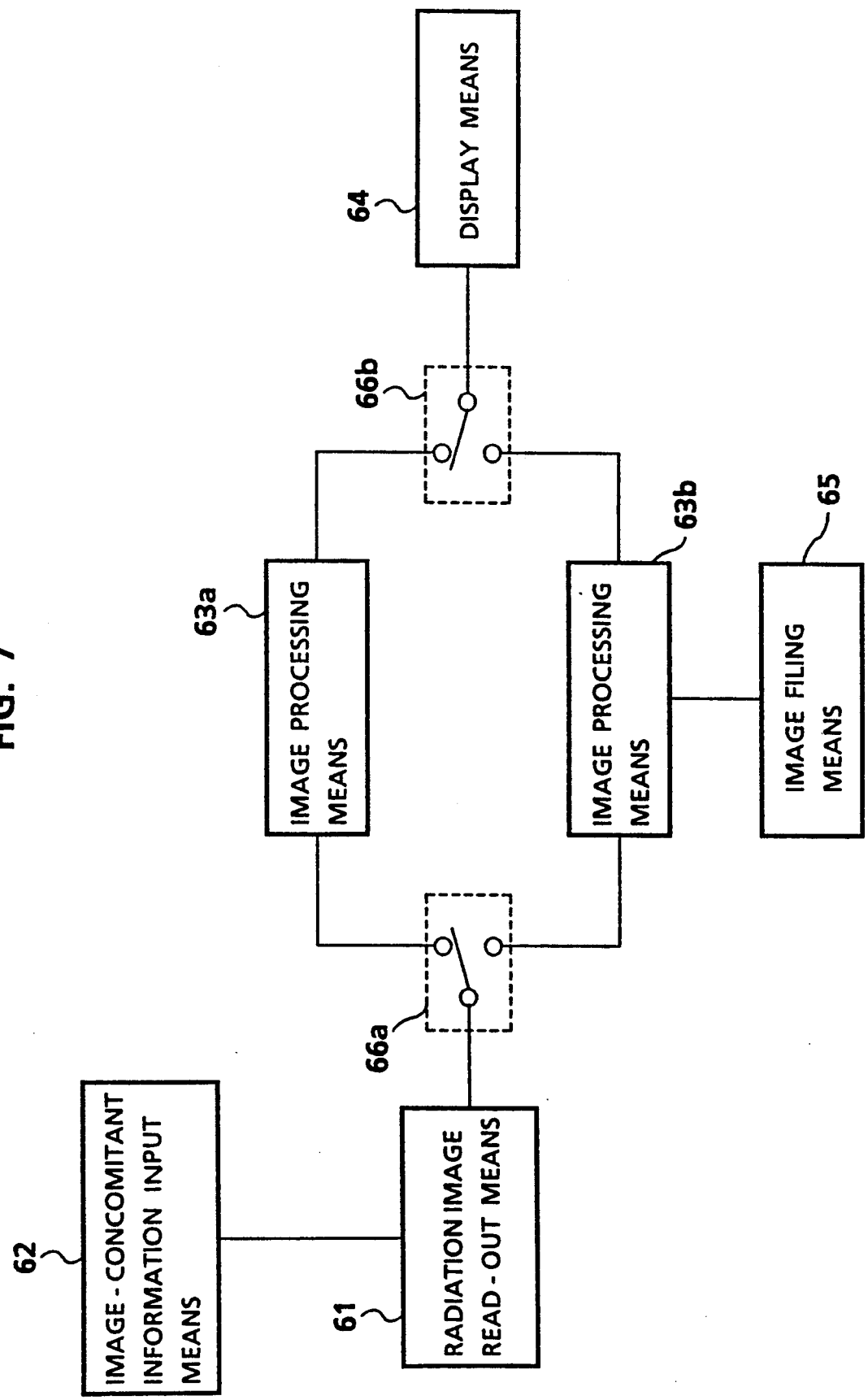
FIG. 7 is a block diagram illustrating the image forwarding-processing controller of FIG. 6 in more detail.

FIG. 7 schematically illustrates more concretely the function of the image forwarding-processing controller means wherein the controller means 66 are divided into two units 66a, 66b. When digital image data and their supplemental data are supplied together from the read-out means 61 to the controller unit 66a, the controller unit 66a studies these data and decides where the digital image data should be forwarded. For instance, the digital image data are forwarded to the image filing means 65 for storing therein, as well as to the image processing means 63a for appropriate processing. The digital image data are processed in the image processing means 63a and then forwarded through the unit 66b to the display means 64. Naturally, other routes for forwarding and processing the digital image data can be chosen.

Figure 8:
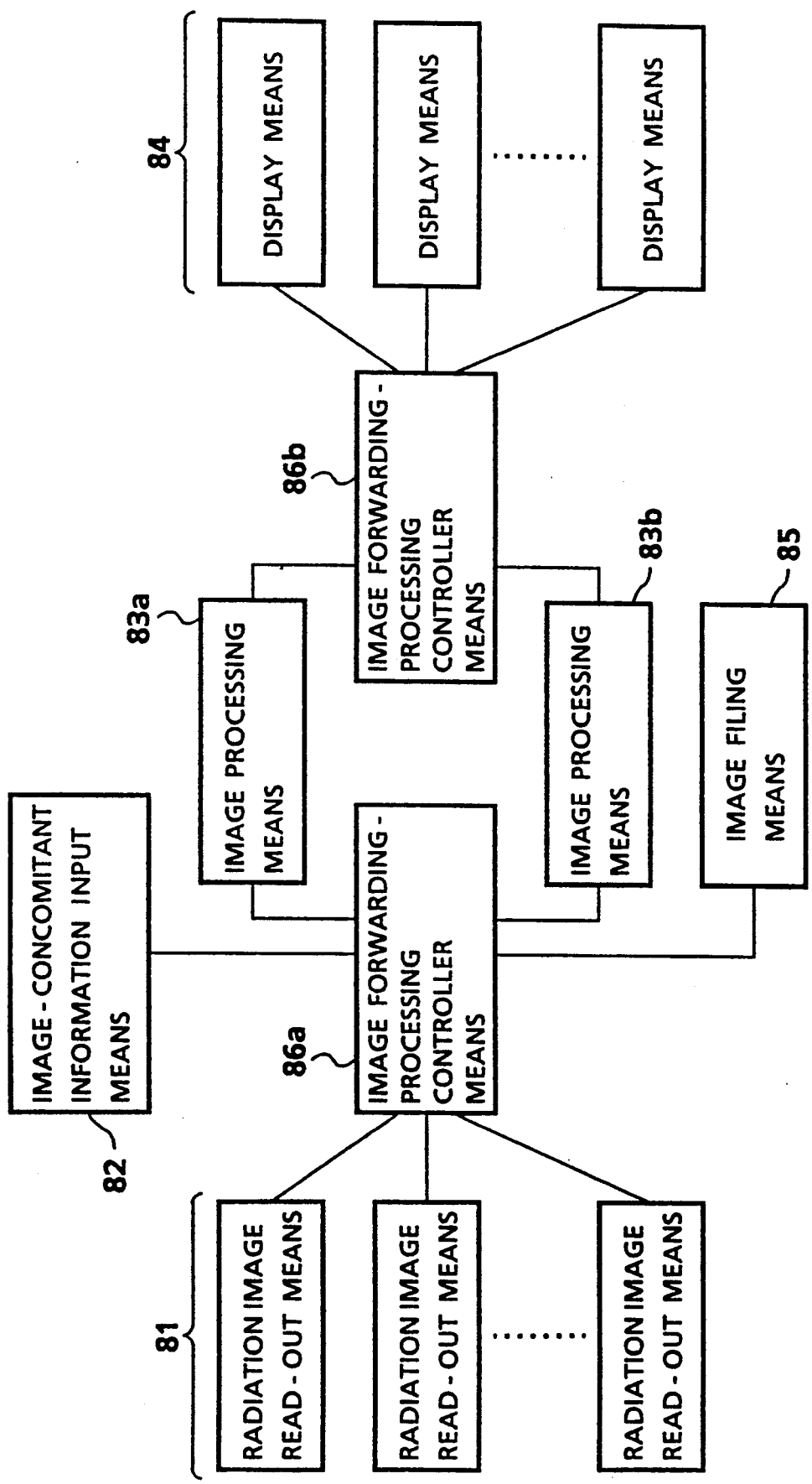
FIG. 8 is a block diagram showing a further embodiment of the radiation image storage and reproduction system of the present invention.

In FIG. 8, one variation of the radiation image storage and reproduction system of the invention is shown. In the system of FIG. 8, a plurality of radiation image read-out means 81, the image-concomitant information input means 82, two image processing means 83a, 83b and the image filing means 85 are connected to the image forwarding-processing controller means 86a. The two image processing means 83a, 83b and a plurality of display means 84 are connected to the image forwarding-processing controller means 86b. The two image forwarding-processing controller means 86a, 86b in combination function in the same manner as described hereinbefore.

What is claimed is:

1. A radiation image storage and reproduction system for medical diagnosis comprising:

radiation image read-out means for reading out a radiation image of a patient stored in a stimulable phosphor sheet to obtain digital image data of the radiation image;

image-concomitant information input means operable for inputting information of a forwarding location and information of an image processing operation for the digital image data;

a plurality of independent image processing means for processing the digital image data, an image processing operation of at least one of the plurality of image processing means being different form an image processing operation of another one of said image processing means;

display means for visually reproducing the radiation image from the digital image data;

image filing means for storing the digital image data; and image forwarding-processing controller means to which the radiation image read-out means, the image-concomitant information input means, the plurality of image processing means, the display means and the image filing means each is connected, each of the plurality of image processing means being independently connected to said image forwarding-processing controller means, said image forwarding-processing controller means being operable for determining a forwarding location of the digital image data based on the information of the forwarding location supplied from said image-concomitant information input means and for forwarding the digital image data to the determined forwarding location, said image forwarding-processing controller also being operable for controlling said image processing means in accordance with the information of the processing operation supplied from said image-concomitant information input means so that suitable image processing means is selected from the plurality of image processing means to process the digital image data according to the supplied processing operation information, said forwarding location representing at least one of said display means, said image filing means and said image processing means.

2. The radiation image storage and reproduction system as claimed in claim 1, wherein a plurality of the radiation image read-out means are included in the system.

3. The radiation image storage and reproduction system as claimed in claim 1, wherein a plurality of the display means are included in the system.

4. A radiation image storage and reproduction system for medical diagnosis comprising:

radiation image read-out means for reading out a radiation image of a patient stored in a stimulable phosphor sheet to obtain digital image data of the radiation image;

image-concomitant information input means operable for inputting information of a forwarding location and information of an image processing operation for the digital image data, said image-concomitant information input means being connected to the radiation image read-out means;

a plurality of independent image processing means for processing the digital image data, an image processing operation of at least one of the plurality of image processing means being different from an image processing operation of another one of the image processing means;

display means for visually reproducing the radiation image from the digital image data;

image filing means for storing the digital image data; and image forwarding-processing controller means to which the radiation image read-out means, the plurality of image processing means, the display means and the image filing means each is connected, each of the plurality of image processing means being independently connected to said image forwarding-processing controller means, said image forwarding-processing controller means being operable for determining a forwarding location of the digital image data based on the information of the forwarding location supplied from said image-concomitant information input means through said radiation image read-out means and for forwarding the digital image data to the determined forwarding location, said image forwarding-processing controller also being operable for controlling said image processing means in accordance with the information of the processing operation supplied from said image-concomitant information input means through said radiation image read-out means so that suitable image processing means is selected from the plurality of image processing means to process the digital image data according to the supplied processing operation information, said forwarding location representing at least one of said display means, said image filing means and said image processing means.

5. The radiation image storage and reproduction system as claimed in claim 4, wherein a plurality of the radiation image read-out means are included in the system.

6. The radiation image storage and reproduction system as claimed in claim 4, wherein a plurality of the display means are included in the system.

7. A radiation image storage and reproduction system for medical diagnosis comprising:

radiation image read-out means for reading out a radiation image of a patient stored in a stimulable phosphor sheet to obtain digital image data of the radiation image;

image-concomitant information input means operable for inputting information of a forwarding location and information of an image processing operation for the digital image data;

a plurality of independent image processing means for processing the digital image data, each of said image processing means having a same image processing function;

display means for visually reproducing the radiation image from the digital image data;

image filing means for storing the digital image data; and image forwarding-processing controller means to which the radiation image read-out means, the image-concomitant information input means, the plurality of image processing means, the display means and the image filing means each is connected, said image forwarding-processing controller means being operable for determining a forwarding location of the digital image data based on the information of the forwarding location supplied from said image-concomitant information input means and for forwarding the digital image data to the determined forwarding location, said image forwarding-processing controller also being operable for controlling said image processing means in accordance with the information of the processing operation supplied from said image-concomitant information input means so that suitable image processing means is selected from the plurality of image processing means to process the digital image data according to the supplied processing operation information, said forwarding location representing at least one of said display means, said image filing means and said image processing means.

8. The radiation image storage and reproduction system as claimed in claim 7, wherein each of the plurality of image processing means is independently connected to said image forwarding-processing controller means.

9. A radiation image storage and reproduction system for medical diagnosis comprising:

radiation image read-out means for reading out a radiation image of a patient stored in a stimulable phosphor sheet to obtain digital image data of the radiation image;

image-concomitant information input means operable for inputting information of a forwarding location and information of an image processing operation for the digital image data, said image-concomitant information input means being connected to the radiation image read-out means;

a plurality of independent image processing means for processing the digital image data, each of said image processing means having a same image processing function;

display means for visually reproducing the radiation image from the digital image data;

image filing means for storing the digital image data; and image forwarding-processing controller means to which the radiation image read-out means, the plurality of image processing means, the display means and the image filing means each is connected, said image forwarding-processing controller means being operable for determining a forwarding location of the digital image data based on the information of the forwarding location supplied from said image-concomitant information input means through said radiation image read-out means and for forwarding the digital image data to the determined forwarding location, said image forwarding-processing controller also being operable for controlling said image processing means in accordance with the information of the processing operation supplied from said image-concomitant information input means through said radiation image read-out means so that suitable image processing means is selected from the plurality of image processing means to produce the digital image data according to the supplied processing operation information, said forwarding location representing at least one of said display means, said image filing means and said image processing means.

10. The radiation image storage and reproduction system as claimed in claim 9, wherein each of the plurality of image processing means is independently connected to said image forwarding-processing controller means.

* * * * *